US012642682B2

(12) United States Patent
Vyas et al.

(10) Patent No.: US 12,642,682 B2
(45) Date of Patent: Jun. 2, 2026

(54) DEVICES AND METHODS FOR THE MANAGEMENT AND PREVENTION OF HERNIA AND OTHER MUSCULOSKELETAL INJURIES

(71) Applicants: Dinesh Vyas, Elk Grove, CA (US); Suresh Subraya Pai, Los Altos, CA (US); Celso Bagaoisan, Union City, CA (US)

(72) Inventors: Dinesh Vyas, Elk Grove, CA (US); Suresh Subraya Pai, Los Altos, CA (US); Celso Bagaoisan, Union City, CA (US)

(73) Assignee: Dinesh Vyas, Elk Grove, CA (US)

( * ) Notice: Subject to any disclaimer, the term of this patent is extended or adjusted under 35 U.S.C. 154(b) by 1371 days.

(21) Appl. No.: 16/940,271

(22) Filed: Jul. 27, 2020

(65) Prior Publication Data

US 2021/0007877 A1    Jan. 14, 2021

Related U.S. Application Data

(63) Continuation of application No. PCT/US2019/016433, filed on Feb. 1, 2019.

(Continued)

(51) Int. Cl.
*A61B 5/103* (2006.01)
*A41D 1/00* (2018.01)

(Continued)

(52) U.S. Cl.
CPC ............... *A61F 5/28* (2013.01); *A41D 1/002* (2013.01); *A41D 13/1281* (2013.01); *A61B 5/103* (2013.01); *A61B 5/1135* (2013.01);

*A61F 5/34* (2013.01); *G08B 21/0453* (2013.01); *A61B 5/01* (2013.01); *A61B 5/0806* (2013.01);

(Continued)

(58) Field of Classification Search
CPC ......... A61B 5/113; A61B 5/7275; A61B 5/11; A61B 5/08; A61B 5/6805; A61B 5/6804; A61B 5/6831; A61N 1/0484; A61N 1/321; A61N 1/36031; A61N 1/36034; A61N 1/36139; A61N 1/3614; A61N 1/36167;

(Continued)

(56) References Cited

U.S. PATENT DOCUMENTS

| | | | |
|---|---|---|---|
| 2004/0116784 A1* | 6/2004 | Gavish ................... | A61B 5/329 600/300 |
| 2011/0054290 A1* | 3/2011 | Derchak ................ | A61B 5/411 600/388 |

(Continued)

*Primary Examiner* — Joseph A Stoklosa
*Assistant Examiner* — Brian M Antiskay
(74) *Attorney, Agent, or Firm* — William A English; Vista IP Law Group LLP

(57) ABSTRACT

Systems and methods are provided for mitigating and/or preventing a hernia using a wearable device worn by a user such that an output device is positioned at a predetermined location corresponding to a target hernia mitigation site on the user's body. One or more physical parameters of the user are monitored to identify when the user is about to perform a predetermined physical activity, and the output device is activated to provide an output to mitigate a hernia or prevent a hernia from occurring at the mitigation site when the predetermined activity is performed.

25 Claims, 4 Drawing Sheets

Related U.S. Application Data

(60) Provisional application No. 62/625,958, filed on Feb. 2, 2018.

(51) Int. Cl.

| | |
|---|---|
| *A41D 13/12* | (2006.01) |
| *A61B 5/05* | (2021.01) |
| *A61B 5/113* | (2006.01) |
| *A61F 5/28* | (2006.01) |
| *A61F 5/34* | (2006.01) |
| *G08B 21/04* | (2006.01) |
| *A61B 5/00* | (2006.01) |
| *A61B 5/01* | (2006.01) |
| *A61B 5/08* | (2006.01) |
| *A61B 5/083* | (2006.01) |
| *A61B 5/145* | (2006.01) |
| *A61B 5/22* | (2006.01) |

(52) U.S. Cl.
CPC ......... *A61B 5/0836* (2013.01); *A61B 5/14542* (2013.01); *A61B 5/22* (2013.01); *A61B 5/4266* (2013.01); *A61B 5/441* (2013.01); *A61B 5/4836* (2013.01); *A61B 5/6804* (2013.01)

(58) Field of Classification Search
CPC ............ A61H 1/008; A61H 2201/0173; A61H 2201/018
USPC ....... 600/372, 382, 384, 386, 388–390, 393, 600/412, 437–439, 484, 488, 529, 534, 600/536, 538; 607/2, 6, 11, 46, 48, 62, 607/98, 108, 115
See application file for complete search history.

(56) References Cited

U.S. PATENT DOCUMENTS

| | | | |
|---|---|---|---|
| 2017/0095670 A1* | 4/2017 | Ghaffari | A61M 21/02 |
| 2018/0160967 A1* | 6/2018 | diMonda | A41D 13/1281 |
| 2018/0214692 A1* | 8/2018 | Esh | A61N 1/36031 |
| 2018/0376586 A1* | 12/2018 | Longinotti-Buitoni | A61B 5/6805 |
| 2022/0023652 A1* | 1/2022 | Schwarz | A61F 7/02 |

* cited by examiner

FIG. 1A                                          FIG. 1B

| Localized Application Site | Neck | Hip | Spine | Shoulder | Upper arm | Fore arm | Wrist | Hand | Finger | Lower leg | Ankle | Foot | Thigh |
|---|---|---|---|---|---|---|---|---|---|---|---|---|---|
| Football | 1 | 1 | 1 | 1 | 1 | 1 | 1 | 1 | 1 | 1 | 1 | 1 | 1 |
| Handball | 1 | 1 | 1 | 1 | 1 | 1 | 1 | 1 | 1 | 1 | 1 | 1 | 1 |
| Office Work | 1 | | 1 | | | | 1 | | | | | | |
| Ski | 1 | 1 | 1 | 1 | 1 | 1 | 1 | 1 | 1 | 1 | 1 | 1 | 1 |
| Biking | | 1 | 1 | 1 | 1 | | | 1 | | 1 | 1 | 1 | 1 |
| Basketball | 1 | 1 | 1 | 1 | 1 | 1 | 1 | 1 | 1 | 1 | 1 | 1 | 1 |
| Gymnastics | 1 | 1 | 1 | 1 | 1 | 1 | 1 | 1 | 1 | 1 | 1 | 1 | 1 |
| Volleyball | | 1 | 1 | 1 | 1 | 1 | 1 | 1 | 1 | 1 | 1 | 1 | 1 |
| Trek and Field | 1 | 1 | 1 | 1 | 1 | 1 | 1 | 1 | 1 | 1 | 1 | 1 | 1 |
| Tennis | 1 | 1 | 1 | 1 | 1 | 1 | 1 | 1 | 1 | 1 | 1 | 1 | 1 |
| Ice skating | 1 | 1 | 1 | 1 | 1 | 1 | 1 | 1 | 1 | 1 | 1 | 1 | 1 |
| Dance | 1 | 1 | 1 | 1 | 1 | 1 | 1 | 1 | 1 | 1 | 1 | 1 | 1 |
| Judo | 1 | 1 | 1 | 1 | 1 | 1 | 1 | 1 | 1 | 1 | 1 | 1 | 1 |
| Swimming | 1 | 1 | 1 | 1 | 1 | 1 | 1 | 1 | | 1 | 1 | 1 | 1 |
| Jogging | | 1 | 1 | 1 | | | | | | 1 | 1 | 1 | 1 |
| Horse riding | 1 | 1 | 1 | 1 | 1 | 1 | 1 | 1 | 1 | 1 | 1 | 1 | 1 |
| Badminton | | 1 | 1 | 1 | 1 | 1 | 1 | 1 | 1 | 1 | 1 | 1 | 1 |
| Wrestling | 1 | 1 | 1 | 1 | 1 | 1 | 1 | 1 | 1 | 1 | 1 | 1 | 1 |
| Inline skating | 1 | 1 | 1 | 1 | 1 | 1 | 1 | 1 | 1 | 1 | 1 | 1 | 1 |
| Skateboard | 1 | 1 | 1 | 1 | 1 | 1 | 1 | 1 | 1 | 1 | 1 | 1 | 1 |

FIG. 4

DEVICES AND METHODS FOR THE MANAGEMENT AND PREVENTION OF HERNIA AND OTHER MUSCULOSKELETAL INJURIES

RELATED APPLICATION DATA

The present application is a continuation of co-pending International application No. PCT/US2019/016433, filed Feb. 1, 2019, which claims benefit of U.S. provisional application Ser. No. 62/625,958, filed Feb. 2, 2018, the entire disclosures of which are expressly incorporated by reference herein.

FIELD OF THE INVENTION

The field of the present invention relates generally to systems, devices, and methods for mitigating or preventing hernias and/or other musculoskeletal injuries, and, more specifically to sensors, electromechanical devices, and/or garments that can work as a system to identify, mitigate or prevent hernias and/or other musculoskeletal injuries.

BACKGROUND

Hernia repair is one of the most common surgical procedures performed globally. It is estimated that there are over twenty million hernia repair procedures per year worldwide. The number of procedures has been increasing and is predicted to further increase due to several risk factors such as obesity and prior abdominal surgeries. Hernia repairs provide an important revenue stream for hospitals, estimated at $48 billion/year in the United States.

Typically hernia defects present from a variety of underlying etiologies. Five percent of the world's population have hernias related to birth (congenital) defects. Another source is trauma induced by surgery. Notably, after colorectal and vascular surgery, the ventral hernia rates can reach 25% of the operated worldwide population. These rates can be even higher in the context of multi-visceral trauma and emergency surgeries. Sometimes the hernia is caused by genetic collagen and other tissue disorders wherein an inhibition of proper collagen crosslinking leads to laxity of fascial planes.

Hernia has a very high occurrence in conditions associated with an overall increased pressure in the abdomen. Often, the causation is due to coughing, exertion, strenuous physical exercise, constipation, prostate related issues, and higher incidence even from ascites associated with cardiac and liver failure. These pressure-related etiologies are widespread and present in very significant percentages across the global population. In general, it is clear that the root cause of herniation is both complex and multifactorial, but increased abdominal pressure appears to be the most significant contributor to eliciting and exacerbating the condition.

Musculoskeletal injuries are the most common ailment affecting every individual multiple times in their lifetime. Musculoskeletal injuries may start from most benign activities, such as sleeping in bad posture, sitting posture, to all sports. The cost of management of musculoskeletal injuries including scans, physiotherapy and surgical management is close to trillion dollars in the United States.

It is also notable that breathing (respiration) itself is a source of hernia formation. Pressure in the abdomen is generated by the contraction of the diaphragm and abdominal muscles. These muscles effectively contract in synchrony to generate intra-abdominal pressures ranging between 300-1200 cm of water. The pressure generated is synchronous with breathing in normal circumstances, but alternatively can also occur somewhat randomly (e.g., when one is taking a deep breath before lifting a barbell) or even continuously in condition like ascites. Sometimes the pressure is almost constant (e.g., when one is undergoing a coughing spell in bronchitis and other exposure related situations).

With this, hernias can develop in a multitude of locations on the human body. Most frequently hernias develop at the inguinal zone or groin. However, hernias also develop frequently in the umbilical area, in the area of surgical trauma (e.g., ventral hernias situated at the incisional site of surgery typically on the center of the abdomen). Less frequently, hernias can develop in the epigastric fascia, femoral fascia, Spigelian fascia and lumbar fascia.

Most all human beings are prone to hernia in one of these regions of the body and certain individuals with the previously mentioned conditions are more prone than others. As would be expected, certain individuals with underlying medical issues have very high chances of developing hernia and often these can be lessened or mitigated or prevented. Further, athletes and sportsmen are always at risk of hernia due to potential over exertion and increased pressure in their muscles with continuous and cumulative shearing of the tissue. These loads can eventually overload the tissue and thereby elicit tearing and herniation.

To that end, there exist a variety of devices intended to prevent herniation that typically include simple mechanical pressure devices like abdominal/hernia belts and trusses. These device solutions are passive (i.e., do not respond to any biofeedback of the wearer). They are low pressure, often ill-positioned and non-calibrated tools with proven almost zero positive outcome. These passive devices are also generally ineffective and typical/almost always fail to prevent or stabilize the hernia.

There are a number of limitations that can be observed and described about these existing passive hernia prevention devices. Typically, the belts are made of an elastic material or a non-compliant leather (or leather like) material and thereby apply a hit or miss load to the target anatomy where the hernia is evolving. As stated previously, such devices also do not react to any biofeedback signal and as a consequence only apply a constant load to the target anatomy. The very nature of these types of these passive devices and how they are positioned on the user's body predispose them to apply very light and relatively ineffective loads on the target anatomy. With use, such passive devices can also lose their shape and structure and further reducing the device efficacy. The reason for this is that, as the shape is lost, the applied force likely diminishes even further and the device may also potentially get displaced or fail to maintain its proper position on or about the anatomical target area where pressure is needed most.

These devices are also not sophisticated and thereby have no means to record, adjust, and/or calculate pressure and, further, they lack mechanisms that allow generation of extra pressure on demand by the user (e.g., during excessive coughing or lifting something very heavy). In general, such devices are devoid of any way of capturing or comprehending the needs of the user's body. As stated previously, most available devices are also not suited for certain anatomical locations where hernias can form. For example, there are few or nonexistent solutions for treatment of lumbar, large ventral or Spigelian hernias.

As such, there exists a need to overcome this wide and varied list of device limitations in the space of mitigation and prevention of hernias.

SUMMARY

Described herein are devices, systems, and methods to mitigate or prevent hernias and/or other musculoskeletal injuries. As explained above, it would be desirable to have a sophisticated or "smart" device that can potentially address and overcome the limitations of existing devices, e.g., passive belts and/or supports. Such a smart device may incorporate a biofeedback mechanism that identifies various sources for initiating synchronized external pressure and/or other localized treatment, e.g., that imparts matching load to the internal pressure (e.g., can take respiration and/or muscle-based feedback and translate this into a force at or about any target anatomy wherein a hernia may occur or form).

For example, embodiments of the systems herein may incorporate feedback from respiration (e.g., dimensional increases in the girth of the chest), sensors detecting biochemical parameters (e.g., from sweat, skin temperature, and the like), or feedback from muscles (e.g., electrical signal feedback from abdominal muscles or from the diaphragm). Alternatively, the feedback may come from observations of changes in respiratory or blood gases (e.g., capnographic or oximetric signals), chemical sensors detecting excessive lactate/myoglobulin and others, or temperature sensors detecting differences within a particular body in comparison to other parts and/or core body temperature. There are other sensors on electrical activity that will also be deployed. The embodiments of the system may translate these feedback signals into almost instantaneous (e.g., less than one millisecond) counteractive applied forces on the herniation zones or other localized anatomy. Such a smart device may also incorporate sensors as required on the chest and/or abdomen of the user to provide objective measure of the forces generated during exertion or coughing and provide a user interface wherein such useful information is clearly displayed for the user.

In general, it would be useful to have a device or a system that generates forces in response to the desired biofeedback mechanism to counteract or neutralize the intra-abdominal force, or activates to prevent muscle contraction or injury, thereby mitigating the propensity of tissue damage and subsequent hernia formation. In one embodiment, on demand of the user, the system may provide constant low pressure, constant high pressure, or alternatively cycled pressure that is either synchronized or delivery asynchronously with the biofeedback signal (e.g., from respiration or other inputs).

It would also be desirable to have a device or system that may apply additive loads either based on the demands of the biofeedback signal (e.g., when the intra-abdominal pressures are higher than nominal or usual) or simply when higher loads are desired or demanded explicitly by the user for whatever reason. In an exemplary embodiment, such a device or system may include a battery operated controller wherein the battery can either be replaced and/or easily recharged using methods commonly seen in other devices like mobile phones or other electronics.

Optionally, the device components of a smart system as described herein may be carried or housed in a unique, athletic (or non-athletic) garment or wearable device that suitably houses or contains the components, e.g., the biofeedback mechanism, sensors, a controller, optionally with a display, a battery and/or other power source, any interconnections between the components, and force generation mechanism. It is envisioned that this type of garment may be worn during athletic activities without impeding desired performance while maintaining optimal positioning of the components on the various anatomical locations of the body. The system components may also be removable for repair or replacement or as required during garment washing.

In addition or alternatively, the devices and systems herein may include a communication interface to provide wireless functionality (e.g., using Bluetooth Low Energy ("BLE") protocols) to transmit information about the system's utilization (e.g., pressure at anatomical target during exertion or coughing or nominally, pressure applied by the system to counteract intra-abdominal pressures, girth measurement of chest, muscle electrical activity, blood gas data, number of cycles applied in synchrony graphical format with any biofeedback signals above, and the like). All such desired data may be sent to a wireless handheld device (e.g., iPhone or Android mobile phone, tablet, or other smart device) and sent to the cloud for further data analysis, e.g., on a pc/laptop or phone based application to (for example) help an athlete improve his/her exercise regimen and/or to prevent injuries.

Similarly, for musculoskeletal injuries, a system may be provided that includes one or more sensors, e.g., for identifying predetermined activities and/or parameters of the user, and one or more output mechanisms as discussed herein to detect and prevent injury. For example, the output may be by transcutaneous electrical stimulation, pressure, ultrasonic, chemical, and others. All the data from the system may be used to develop machine learning for personalized care of the user. In addition, the interface may see images of the activity, e.g., using ultrasound imaging and/or electrical impulses, translated into simplified images. The images may be translated into user-friendly images, e.g., that may be presented on a remote electronic device, e.g., a tablet, mobile phone, computer, and the like, for use by the user and/or the user's physician, trainer, and the like.

In accordance with one embodiment, a hernia device or system is provided that includes a sensor mechanism configured to measure the amount or change in physical dimension (e.g., dimensional increase in the girth of the chest) and/or force exerted by the muscle during respiration; a controller that receives signal or information from the sensor mechanism and processes that information to send a signal or command to peripheral components of the system; a pressure applicator located at one or more anatomical locations at risk of forming a hernia or aggravating a healing hernia or preventing the occurrence of existing hernia to apply a focal load at the one or more locations; and a wearable garment that encloses or supports the various components of the hernia device. Additional components may be included, such as power sources, control mechanisms (electronic and/or mechanical), switches, valves, flow directing components, housings, actuators, and the like, as part of each of the components of the system.

In accordance with another embodiment, a hernia device may be provided that includes a sensor (i.e., sensing mechanism), which may be secured about the ribcage, chest or other body location of the subject user and/or may be attached to or integrated with a flexible or rigid band. For example, the sensor may include a mechanism that generates an electrical signal in response to the change in ribcage and/or diaphragm perimeter during inhalation and exhalation. The sensor may be configured such that the strength of the electrical signal is proportional to the relative expansion of the ribcage and/or diaphragm (e.g., electrical signal increases as the dimension increases from chest expansion and vice versa).

Specific examples of sensors that may be used with the system may be fabricated from commercially available materials including, but not limited, to a resistive flex sensor and/or conductive rubber chord sensor that changes its resistance by changing its form or configuration such as flexing and/or stretching. The system may be configured such that the value of resistance is proportional to the relative expansion of the ribcage and/or diaphragm (e.g., the resistance increases as the dimension increases from chest expansion and vice versa).

Another example of a sensor is a pressure sensitive conductive sheet that changes the resistance by applying pressure or by squeezing the sheet during respiration. The change in resistance can be induced by and can be correlated to the relative force exerted by the underlying muscle (e.g., resistance increases as the user exerts more energy and vice versa). Another type of sensor that may be used is a capnographic or oximetric sensor that detects respiratory or blood gasses, such as a change in oxygen or carbon dioxide levels in relation to the level of physical exertion during intense workout or exercise.

Yet another example of a sensing mechanism is a bladder structure or a flexible band equipped with a transducer that measures pressure when the bladder structure is compressed. The change in pressure can be induced by and can be correlated to the relative expansion of the ribcage and/or diaphragm (e.g., the pressure increases as the user's girth expands and vice versa). The flexible band may be fabricated from materials known to the art including, but not limited to cotton, nylon, wool, latex, natural rubber, elastane (Lycra®), silk, microfiber, composite materials such as a polymer that incorporates resistive or conductive materials, combinations thereof, and the like. For example, the property (e.g., texture, elasticity) of the flexible band may be modified along different portions of the band by adjusting the speed and/or tension of the knitting operation that is used to create the fabric of the band, the relative percentage of the differing materials used in varying portions of the band, the weight of the fibers used in the knitting of varying portions of the band, and the like.

The band may exhibit consistent or varied parameters along the differing dimensions of the band; such parameters may include, but are not limited to material composition, tensile strength, elasticity, band width, band thickness, color, texture, gas permeability, liquid permeability, and the like. The band may be secured to itself using closures known to those of skill in the art including, but not limited to hook-and-loop fasteners, hooks and eye closures, toggle closures, ties, cord laced through grommets, zippers, snaps, buttons, buckles, side-release buckles, combinations thereof, and the like.

The flexible band may further comprise a sensing mechanism capable of detecting the expansion of the user's ribcage and/or diaphragm. This sensor may be permanently or reversibly attached to the flexible band. The flexible band may also be incorporated into a garment such as jersey, shirt, singlet or the like.

Optionally, in any of the embodiments herein, the sensor or sensing mechanism may be connected to and/or communicate with a controller, e.g., via a wired connection or may be remotely connected via wireless communication, e.g., using BLE signals. The controller is essentially the main brain of the system wherein the peripheral components (e.g., sensor or sensing mechanism, pressure applicator, valves, switches, etc.) are connected to, controlled by, and/or communicate via the controller. For example, the controller may be configured to receive signals generated by the sensor or sensing mechanism and process, record, modify, and/or transmit the signals, e.g., issuing one or more commands to other peripheral components based on the signals.

In one example, the controller may record the signals from the sensor when a user is at rest to establish a baseline range that is unique to the user. The controller may further record subsequent signals from the sensor, e.g., to identify when the user is undergoing aggressive levels of physical activity. The controller may allow the user to set a trigger level based off of a comparison between the two signals, e.g., to establish a predetermined threshold or trigger whereupon a correcting action is taken. This process may serve to calibrate the sensor and/or the controller to the unique physical responses of individual users. It should be understood that the signals may be transformed or conditioned prior to, during, or after conducting the comparison. These transformation techniques may include, but are not limited to, averaging the sum total value of the signal over a given length of time, performing a moving average window filter on the signal, applying a high pass, low pass, or bandpass filter to the data, increasing or decreasing the gain of the signal, calculating the position or derivatives thereof (e.g., velocity, acceleration, jerk) of the expansion of the user's ribcage and/or diaphragm, combinations thereof, and the like.

For example, the user may choose to set a trigger value at 70% of the peak signal produced during aggressive exercise. The controller would then take one or more actions once the trigger value is exceeded. It should be clear to those of skill in the art that many conditional instructions and processes may be monitored by the controller, such as only taking action if the trigger value is exceeded and the acceleration of the signal is below a second trigger value. This may represent a state in which the user has slowly inhaled and fully expanded their chest cavity in preparation for conducting an athletic movement that requires significant abdominal support. A set of rules or conditions of this nature would prevent the controller from taking action if, for example, the user rapidly inhales due to surprise or another unintended response or action.

In addition or alternatively, the controller may be configured to provide a lower level of support over extended time durations. For example, the trigger value may be set low enough to permanently activate the system, or the controller may include a shutoff mechanism to optionally disable the input of the sensing mechanism and manually activate the system. These variations may provide assistance in other treatment areas, such as the treatment of ventral, umbilical, or Spigelian hernias, or the prophylactic treatment of inguinal ring hernias during non-aggressive activities.

The controller may be fabricated from and/or may include materials and components known to the art, such as electronic hardware including one or more circuit board assemblies comprising commercially available electronic and mechanical components (e.g., integrated circuits/chips, EPROM, resistors, transistors, capacitors, potentiometers, relays, switches, antenna, terminals, etc.) and may be configured into a compact unit. The circuit board assembly may be enclosed within an ergonomic enclosure that may include one or more externally accessible components (e.g., a LCD display, switch, button, and the like) that allows the user to operate and/or control the various modes of function of the device. Furthermore, the controller may include firmware that is configured or programmed to process the signals and/or feedback coming from the sensor and other peripheral components of the system, after which, it may further send signals or commands back to the sensor and/or other peripheral components of the system.

The controller may be powered by a rechargeable or replaceable power source. The power source may be in the same physical location as the controller, or may be separate from and connected to the controller via a wired connection. The controller may have design elements that allows communication to peripheral components wirelessly (e.g., using Bluetooth Low Energy or other communications protocols) and/or may have the capability to transmit or receive signals from the peripheral components. The controller may also have the capability to transmit or receive data using high-speed wireless telecommunication to remote devices, such as mobile devices, i-cloud or remote data storage, medical service provider's beeper, and the like.

The hernia device may also include one or more pressure applicators that directly apply pressure to the inguinal ring or other select anatomical locations of the body that are at risk where a hernia may occur or may need to be managed. This pressure applicator may be activated pneumatically, hydraulically, electromagnetically, mechanically, combinations thereof, and the like. For example, the pressure applicator may comprise a reservoir containing an incompressible fluid and a bladder. The bladder and the reservoir may be in fluid communication with each other via the use of rigid or flexible tubing with at least one lumen, and flow between the reservoir and the bladder may be controlled via the use of a valve or system of valves known in the art including, but not limited to solenoid valves, check valves, duckbill valves, ball and spring valves, flapper valves, combinations thereof, and the like. The pressure applicator may further comprise a pumping mechanism that can drive fluid between the reservoir and the bladder.

For example, the pumping mechanism may include comprise a mechanical pump or device for compressing a flexible, elastic, or collapsible reservoir to increase the internal pressure within the reservoir. One example of such a mechanism is the use of a syringe as the reservoir combined with a mechanism to depress the syringe plunger. Depressing the syringe plunger will increase pressure in the syringe and direct fluid from the syringe into the bladder. The mechanism of depressing the syringe plunger may be mechanical (e.g., a compressed spring, a rack and pinion arrangement, etc.), pneumatic (e.g., use of a compressed gas cylinder), hydraulic, combinations thereof, and the like.

Alternatively, the pressure applicator may include a positive displacement pump including but not limited to internal gear pumps, screw pumps, shuttle block pumps, flexible vane pumps, sliding vane pumps, circumferential piston pumps, flexible impeller pumps, helical twisted root pumps, liquid-ring pumps, peristaltic pumps, piston pumps, plunger pumps, diaphragm pumps, air pump, and the like. The positive displacement pump may be located within or external to the reservoir. The bladder may be filled with fluid and expanded by opening the valve or system of valves between the reservoir and the bladder and engaging or activating the mechanical pumping mechanism.

Optionally, the pressure applicator may further include at least one pressure sensor (e.g., pressure transducer) that can relay information on the pressure within the reservoir and/or bladder to the controller. The controller may then use a control loop, such as a negative feedback loop, to rapidly drive the pressure within the reservoir and/or bladder to a predetermined set point or range of values. Furthermore, the pumping mechanism may be able to reverse the direction of flow to empty the fluid from the bladder and return it to the reservoir. This may be done by reversing the operating orientation of the pump itself, or by manipulating a system of valves and flow paths comprising rigid or flexible tubing with at least one lumen connecting the reservoir, the pump, and the bladder.

Alternatively, the pressure applicator may include a pneumatic mechanism for increasing the internal pressure of the reservoir such as a container of compressed gas that is in fluid communication with the reservoir; flow between the container and the reservoir is controlled via the use of a valve or system of valves known in the art including, but not limited to solenoid valves, check valves, duckbill valves, ball and spring valves, flapper valves, combinations thereof, and the like.

In one embodiment, a system for preventing or treating hernias of the inguinal ring of this type may include three pressure vessels, a controller, a power source, a mechanism of sensing the state of the users ribcage/diaphragm, wires, tubing, and valves connecting the components, and a garment wearable by the user that enables application of pressure to the inguinal ring on either the left or right side of the user's body. The three pressure vessels may include 1) a vessel enclosing and containing a compressed gas, herein referred to as a gas canister, 2) a vessel with substantially rigid walls containing a volume of incompressible fluid, herein referred to as a tank, and 3) a vessel that may receive an incompressible fluid to transition from a collapsed state to an expanded state, herein referred to as a bladder. The bladder is positioned within the garment such that it applies pressure to either the left or right inguinal ring of the user in the expanded state.

The tubing in this example includes an elongate member with proximal and distal ends and at least one lumen there through that provides fluid communication between the proximal and distal ends. The tubing may be flexible, rigid, or of a durometer between those two extremes. It should be clear to one of skill in the art that the size and cross-section of the tubing may to adapted to a particular or specific design of the system and is not restricted to a single geometry or even a set of geometries. In this specific example, the gas canister is connected to the tank via a flow path that includes one or more lengths of tubing, a solenoid valve, and a one-way valve. The solenoid valve and one-way valve are in series, and the one-way valve is oriented such that flow is only permitted from the gas canister into the tank. The solenoid valve, herein referred to as the CT valve, is connected to and governed by the controller. The tank contains an incompressible fluid and further includes a pressure sensor and a relief valve assembly. The pressure sensor is connected to the controller and provides a signal that is proportional to the pressure within the tank.

The relief valve assembly may include one or more lengths of tubing, a solenoid valve, and a filter permeable to gas but not to the incompressible fluid. For example, a length of tubing connects the tank to the filter, and a second length of tubing connects the filter to the solenoid valve. The solenoid valve, herein referred to as the "TE" valve, is connected to and governed by the controller and the distal (away from the tank) side of the solenoid valve is open to the ambient environment.

Additionally, the tank is connected to the bladder via a flow path that includes one or more lengths of tubing, a solenoid valve, and a one-way valve. The solenoid valve and one-way valve are in series, and the one-way valve is oriented such that flow is only permitted from the tank into the bladder. The solenoid valve, herein referred to as the "TB" valve, is connected to and governed by the controller. The bladder further includes a pressure sensor that is connected to the controller and provides a signal that is relative to the pressure within the bladder. A fluid return path that includes one or more lengths of tubing, a solenoid valve, and a one-way valve connects the bladder and tank. The solenoid valve and one-way valve are in series, and the one-way valve is oriented such that flow is only permitted from the bladder into the tank. The solenoid valve, herein referred to as the "BT" valve, is connected to and governed by the controller. The controller is connected to the power source, the solenoid valves, the pressure sensors, and the mechanism of sensing the state of the users ribcage/diaphragm via means of communicating or transmitting electrical power or signals.

The pressure applicator may act to selectively apply pressure to the inguinal ring of the user during times of significant exertion. For example, the user may inhale deeply prior to attempting an athletic movement or act. The increase in girth dimension (i.e., perimeter of ribcage or chest) causes a change in the signals sent by the sensor to the controller, which identifies the change and, consequently, opens the CT solenoid valve to pressurize the incompressible fluid contained within the tank. The controller may optionally regulate the pressure within the tank by comparing the tank pressure as reported by the tank pressure sensor to a pre-selected set point.

If the pressure exceeds the set point, the CT valve may be closed and the TE valve opened to vent a portion of the gas to the environment and reduce the tank pressure. The controller may use a negative feedback loop to quickly bring the tank pressure to the specified set point, or into a band of acceptable pressure values about the set point. The controller may then close the CT and TE valves to isolate the tank from the gas canister and the ambient environment. The TB valve may then be opened to allow flow of the incompressible fluid from the tank into the bladder. The controller may optionally regulate the pressure within the bladder by comparing the bladder pressure as reported by the bladder pressure sensor to a pre-selected set point. If the pressure still exceeds the set point, the TB valve may be closed and the BT valve opened to return a portion of the incompressible fluid to the tank and reduce the bladder pressure. The controller may use a negative feedback loop to quickly bring the bladder pressure to the specified set point, or into a band of acceptable pressure values about the set point.

The bladder will expand upon filling with the incompressible fluid and in turn apply pressure to the inguinal ring of the user. The BT valve may then be closed to maintain the desired bladder pressure for a set amount of time. Once the desired treatment time has been met, the BT valve may be opened to allow the incompressible fluid to flow back into the tank. Optionally, the TE valve may be opened to bring the system into equilibrium with the ambient pressure. Once in equilibrium, all the valves in the system may be closed in anticipation of the next use of the system.

One variation for operating the system would be to pre-pressurize the tank prior to receiving an activation signal from the sensing mechanism. This may be considered as a way to reduce the time needed to apply pressure to the inguinal ring once the activation signal has been received.

While this example describes the use of the hernia device to apply pressure to either the right or left inguinal ring of the user, it should be clear to one of skill in the art that a similar system may be used to apply pressure to both inguinal rings of a user, or to apply pressure to other body surfaces, such as in the management of a ventral, umbilical, or Spigelian hernia. The size, position, number, and target internal pressures of the bladders may be adjusted to treat each specific indication, either prophylactically or as part of a post-hernia treatment regimen as directed by physician (based on patient's baseline tissue).

Furthermore, it should be clear to one of skill in the art that the specific configurations of the gas canister and tank may be altered to suit the particular application of the system and still comply with the general precepts described herein. For example, a tank that is integrated into a backpack may provide a much larger volume of fluid for the bladder than a tank that is integrated into the hip portion of a form fitting athletic or support garment. Alternatively, a more intricate system may include multiple gas canisters and multiple bladders linked to individual tanks, or multiple bladders linked to a single tank in series, parallel, or a combination of the two, or multiple gas canisters connected to multiple tanks in series, parallel, or a combination of the two. Likewise, the controller, power source, sensing mechanism, and bladder or bladders may be configured in a way that accommodates a specific use of the system.

In another exemplary configuration of a system including a pneumatically driven pumping mechanism, the gas canister may be in fluid communication with an elastic enclosure disposed within a tank, e.g., similar to the previous example. For example, an elastic wall may bisect the tank and create two distinct cells within the tank. The size of the cells may be identical or unequal. The elastic wall is impermeable to both the gas and the incompressible fluid. One cell, herein known as the "fluid cell" is filled with an incompressible fluid, and the other, herein known as the "gas cell" is connected to the gas canister via a flow path that incorporates one or more lengths of tubing, a solenoid valve, and a one-way valve.

In this embodiment, the solenoid valve and one-way valve are in series, and the one-way valve is oriented such that flow is only permitted from the gas canister into the fuel cell. The solenoid valve, herein referred to as the CGC valve, is connected to and governed by the controller. The gas cell further includes a pressure sensor and a relief valve assembly. The pressure sensor is connected to the controller and provides signals that are proportional to the pressure within the gas cell. The relief valve assembly includes one or more lengths of tubing, a solenoid valve, and a filter permeable to gas but not to the incompressible fluid.

A length of tubing connects the tank to the filter, and a second length of tubing connects the filter to the solenoid valve. The solenoid valve, herein referred to as the GCE valve, is connected to and governed by the controller and the distal (away from the gas cell) side of the solenoid valve is open to the ambient environment. The fluid cell is connected to the bladder via a flow path that incorporates several lengths of tubing, a solenoid valve, and a one-way valve. The solenoid valve and one-way valve are in series, and the one-way valve is oriented such that flow is only permitted from the tank into the bladder. The solenoid valve, herein referred to as the FCB valve, is connected to and governed by the controller. The bladder further comprises a pressure sensor that is connected to the controller and provides a signal that is relative to the pressure within the bladder.

The system also includes a fluid return path that includes one or more lengths of tubing, a solenoid valve, and a one-way valve connects the bladder and tank. The solenoid valve and one-way valve are in series, and the one-way valve is oriented such that flow is only permitted from the bladder into the tank. The solenoid valve, herein referred to as the BFC valve, is connected to and governed by the controller. The controller is connected to the power source, the solenoid valves, the pressure sensors, and a mechanism for sensing the state of the users ribcage/diaphragm that involves communicating or transmitting electrical power or signals.

The system may act to selectively apply pressure to the inguinal ring of the user during times of significant exertion based on desired settings. For example, the user may inhale deeply prior to attempting an athletic movement or act. The controller may receive signals from one or more sensors, e.g., identifying an increase in girth dimension (i.e., perimeter) of the ribcage or chest, changes in gas reading in the user's blood and/or airway, or local electrical changes causes a sensor and, in response to the signals, the controller may open the CGC solenoid valve to pressurize the gas cell. The controller may optionally regulate the pressure within the gas cell by comparing the gas cell pressure as reported by the gas cell pressure sensor to a pre-selected set point. If the pressure exceeds the set point, the CGC valve may be closed and the GCE valve opened to vent a portion of the gas to the environment and reduce the gas cell pressure.

The controller may use a negative feedback loop to quickly bring the gas cell pressure to the specified set point, or into a band of acceptable pressure values about the set point. The controller may then close the CGC and GCE valves to isolate the gas cell from the gas canister and the ambient environment. The FCB valve may then be opened, enabling the elastic membrane bisecting the tank to expand under the elevated pressure in the gas cell and providing the force to direct flow of the incompressible fluid from the fluid cell into the bladder. The controller may optionally regulate the pressure within the bladder by comparing the bladder pressure as reported by the bladder pressure sensor to a pre-selected set point. If the pressure exceeds the set point, the FCB valve may be closed and the BFC valve opened to return a portion of the incompressible fluid to the fuel cell and reduce the bladder pressure. The controller may use a negative feedback loop to quickly bring the bladder pressure to the specified set point, or into a band of acceptable pressure values about the set point.

The bladder will expand upon filling with the incompressible fluid and, in turn, apply pressure to the inguinal ring of the user. The FCB and BFC valves may then be closed to maintain the desired bladder pressure for a set amount of time. Once the desired treatment time has been met, the BFC valve may be opened to allow the incompressible fluid to flow back into the fluid cell. Optionally, the GCE valve may be opened to bring the system into equilibrium with the ambient pressure.

Once in equilibrium, all the valves in the system may be closed in anticipation of the next use of the system. One variation for using the system would be to pre-pressurize the gas cell before receiving an activation signal from the sensing mechanism. This may be considered as a way to reduce the time needed to apply pressure to the inguinal ring once the activation signal has been received.

In another exemplary system, the bisecting membrane may be replaced by a flexible enclosure fabricated of a gas and fluid impermeable material connected to the gas canister but enclosed within the tank. In this system, the flexible enclosure creates a gas cell that is surrounded by the fluid cell and an expansion of the flexible enclosure applies pressure to the fluid enclosed within the fluid cell. It should be clear to one of skill in the art that the specific configurations of the gas and fluid cells may be altered to suit the particular application of the system and still comply with the general precepts described herein. For example, a tank that is integrated into a backpack may provide a much larger volume for the fluid and gas cells than a tank that is integrated into the hip portion of a form fitting athletic or support garment. Alternatively, a more intricate system may comprise multiple bladders linked to individual tanks, or multiple bladders linked to a single tank in series, parallel, or a combination of the two. Likewise, the controller, power source, sensing mechanism, and bladder or bladders may be configured in a way that accommodates a specific use of the system.

Another exemplary configuration of the system includes a gas canister in fluid communication with a bladder via a flow path that includes one or more lengths of tubing, a solenoid valve, and a one-way valve. The solenoid valve and one-way valve are in series, and the one-way valve is oriented such that flow is only permitted from the gas canister into the bladder. The solenoid valve, herein referred to as the GB valve, is connected to and governed by the controller. The bladder further includes a pressure sensor and a relief valve assembly. The pressure sensor is connected to the controller and provides a signal that is relative to the pressure within the bladder. The relief valve assembly includes one or more lengths of tubing, a solenoid valve, and a filter permeable to gas but not to the incompressible fluid. A length of tubing connects the tank to the filter, and a second length of tubing connects the filter to the solenoid valve. The solenoid valve, herein referred to as the BE valve, is connected to and governed by the controller and the distal (away from the bladder) side of the solenoid valve is open to the ambient environment.

The system may act to selectively apply pressure to the inguinal ring of the user during times of significant exertion. For example, the user may inhale deeply prior to attempting an athletic movement or act. The increase in girth dimension (i.e., perimeter of ribcage) may change signals from a sensing mechanism sent to the controller, which in turn opens the GB solenoid valve to pressurize the bladder. The bladder will expand upon filling with the gas and in turn apply pressure to the inguinal ring of the user. The controller may optionally regulate the pressure within the bladder by comparing the bladder pressure as reported by the bladder pressure sensor to a pre-selected set point. If the pressure exceeds the set point, the GB valve may be closed and the BE valve opened to vent a portion of the gas to the environment and reduce the bladder pressure. The controller may use a negative feedback loop to quickly bring the bladder pressure to the specified set point, or into a band of acceptable pressure values about the set point.

The controller may then close the GB and BE valves to isolate the bladder from the gas canister and the ambient environment to maintain the desired bladder pressure for a set amount of time. Once the desired treatment time has been met, the BE valve may be opened to bring the system into equilibrium with the ambient pressure. Once in equilibrium, all the valves in the system may be closed in anticipation of the next use of the system.

It should be clear to one of skill in the art that the specific configurations of the gas canister and bladders may be altered to suit the particular application of the invention and still comply with the general precepts of the invention. For example, a gas canister that is integrated into a backpack may provide a much larger volume of compressed gas to inflate a bladder than a gas canister that is integrated into the hip portion of a form fitting athletic or support garment. Alternatively, a more intricate system may include multiple bladders linked to gas canisters, or multiple bladders linked to a single gas canister in series, parallel, or a combination of the two. Likewise, the controller, power source, sensing mechanism, bladder or bladders, and wearable garment may be configured in a way that accommodates a specific use of the system.

Other mechanisms of applying pressure to the target anatomical zone or location of the user include the use of an electromechanical solenoid comprising an electromagnetically inductive coil wound around a movable steel or iron armature and connected to a source of electrical current. The coil is shaped such that the armature may be moved in and out of the center, altering the coil's inductance and thereby becoming an electromagnet. The force applied to the armature is proportional to the change in inductance of the coil with respect to the change in position of the armature and the current flowing through the coil. The force applied to the armature moves the armature in a direction that increases the coil's inductance. Once the current is halted, a return mechanism such as an extension or tension spring joined to one end of the armature, can re-seat the armature back in the center of the inductive coil.

A hernia device system capable of selectively applying pressure to the inguinal ring, or another anatomical location of the user, may include a mechanism for sensing the expansion of the user's ribcage/diaphragm, a controller, a power source, and an electromechanical solenoid unit housed on or within a garment wearable by the user. An increase in the perimeter of the user's ribcage/diaphragm causes changes in signals from the sensing mechanism sent to the controller, which in turn applies a current to the electromechanical solenoid to apply pressure to a target anatomical zone or location of the user. The number of electromechanical solenoids may be adapted to the needs of a particular application, such as the post-surgical mitigation or management of ventral hernias, or as part of a maintenance therapy following the surgical treatment of a inguinal ring hernia, or as a prophylactic treatment aimed at preventing various types of hernias.

For example, the management of ventral hernias may require the use of several electromechanical solenoids connected in parallel to a single controller that apply a low level of pressure to the user over an extended amount of time. Alternatively, the prophylactic management of potential inguinal ring hernias may require a single electromechanical solenoid positioned over the right and left inguinal rings of the user. It should be clear to one of skill in the art that any number of electromechanical solenoids may be combined in parallel, series, or a combination thereof, with one or more controllers and sensing mechanisms to realize a system capable of addressing a variety of management modalities for a given user.

The pressure applicator may further include one or more components, such as a pressure head, that may effectively direct and focus the force applied by the expanding bladder or electromechanical solenoid to a specific zone or location of the user's body. The pressure head may be configured as a conical or wedge-like shape structure that has a flat or conical faces or surfaces on opposite ends, with one end having a surface area greater than the other end. One end of the pressure head, for example, the narrow end of the pressure head, may be oriented to be in contact with the target anatomical zone or location of the user's body and the other end (i.e., wider end) may be attached or connected to the bladder or solenoid. When the bladder or solenoid is activated, the pressure head advances and is pushed towards the target treatment zone or location and applies opposing force to counteract the outward force produced by, for example, an intra-abdominal pressures produced during significant exertion or heavy workout session (e.g., weight lifting, etc.).

The pressure head essentially provides focused forced concentrated on the anatomical zone or location of interest. The contact surface of the pressure head may be sized and configured to accommodate and generally be compatible with the specific anatomical target zone or location of the user's body. For example, the zone or location of inguinal ring where hernia may occur may require a pressure head contact diameter range of 0.5 inch to 2.0 inches (12-50 mm), for example, 1.0 inch (25 mm). The pressure head may be fabricated using materials known in the art including, but not limited to metals, polymers/plastics, composites, and combinations thereof. It should be clear to one of skill in the art that any number of forms (e.g., solid, hollow, foam), shapes (e.g., rectangular, spherical, pyramid, octagonal), configurations (e.g., number of contacting surface such as more than one contact points), properties (e.g., hard, soft, compliant) and combinations thereof may be arranged and utilized for the pressure applicator with the aim of effectively and comfortably applying load or force and with sufficient surface area coverage to the target anatomical zone or location of the user's body.

For example, the pressure head may be a hard plastic material with a soft liner or padding incorporated at the outside surface that contacts the user's body in order to provide an atraumatic surface that prevents injury such as blisters, cuts, abrasions or bruising from occurring. Alternatively, a pressure sensitive conductive sheet sensor may be placed as a padding at the interface of the pressure head that makes contact with the user's body so that the pressure applied may also be measured by the sensor by acquiring the change in generated resistance and that information or signal may then be fed back to the controller for further processing to determine the status whether sufficient amount of counter force is being applied in relation to the user's intra-abdominal pressure generated as the user exerts physical activity. The controller may then make instantaneous adjustment or adjustments to the pressure applicator to apply a force that is within the specified value or acceptable range of specified value or parameter. This type of adjustment may be particularly important in certain conditions such as differences in body habitat (i.e., obese versus normal versus thin user), variability in securing the sensor (i.e., tightness) if an adjustable band, belt, or truss is used, compliance or loosening of the band, belt, or truss that is holding the sensor, including all other scenarios that essentially changes the original baseline force parameter gathered by the controller during the initial setup or placement of the sensor.

In accordance with another embodiment of a hernia device or system, the controller and/or other peripheral components of the system (i.e., sensors, pressure applicators, flexible bands, power source(s), interconnections, etc.) may be contained permanently or may reversibly be attached in a wearable garment including a single or multiple pieces of garment, such as those used by athletes or by users performing physical activities such as work outs, trainings or exercises. Optionally, the garment may further include one or more pockets, straps, supporting belts or trusses, flexible bands, snaps, anchors, and/or other suitable design elements or methods that allow for those components to be secured in the garment. The components held by or contained in the wearable garment may be permanently secured or may be removed to allow washing or cleaning of the garment, replacing, repairing and/or maintaining a component, or to simply wear the garment when the user is not involved in any physical activities.

In exemplary embodiments, the garment may be fabricated in various forms of sportswear such as shorts, tracksuits, swimsuits, wet suits, leotards, jockstraps, sports bras, and the like. The garment material may be fabricated using materials commonly used and commercially available fabrics, such as Lycra or elastene (i.e., Spandex), and the like, and may incorporate properties that generally provide comfort to the user. The design, form, type, and/or material used for fabricating the wearable garment containing the components of the hernia device or system are taken into account so that the resulting garment does not diminish the performance of the user or does not impede the user from performing the desired physical activities.

Optionally, the wearable garment may further include a stabilizing element such as a belt, band, or support truss, which may be integrated with or may be a separate piece that may be reversibly attached with the garment. The stabilizing element may be designed to hold or secure the sensor and/or pressure applicator to keep these components from being displaced and to maintain their position relative to the target anatomical zone or location, even during performance of extensive physical activities by the user. The stabilizing element may be fabricated using materials commonly used and commercially available materials, such as reinforced fabric, leather, flexible polymers that has very low elongation properties, combinations thereof, and the like. Such materials may have properties that resist stretching and remain dimensionally stable (e.g., no or negligible change in length or perimeter of the band, belt, or truss) throughout the duration of use, regardless of the environmental condition or atmosphere the stabilizing element is subjected to.

It should be clear to one of skill in the art that aspects of several of these exemplary embodiments may be combined into a single system. For example, a primary pressure system may include a pneumatic pump moving an incompressible fluid to apply one amount of pressure to a specific anatomical location or locations, while a secondary pressure system may include the direct pneumatic inflation of a bladder or bladders to apply a different amount of pressure to a different anatomical location or locations at the same time. The primary and secondary systems may be controlled by a single controller, or by separate controllers that receive an input signal from the sensing mechanism. Alternatively, the secondary system may provide a baseline level of pressure to a specific anatomical location or locations, while the primary system supplements the secondary system at specified or triggered intervals to apply elevated amounts of pressure to the same or different anatomical location or locations.

Other aspects and features including the need for and use of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It is emphasized that, according to common practice, the various features and design elements of the drawings are not to-scale. On the contrary, the dimensions of the various features and design elements are arbitrarily expanded or reduced for clarity. Included in the drawings are the following figures.

FIG. 4 is a table showing an exemplary list of physical activities and potential mitigation sites for applying pressure, stimulation, and/or other treatment.

DETAILED DESCRIPTION OF THE EXEMPLARY EMBODIMENTS

Before the exemplary embodiments are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

Figure 1:
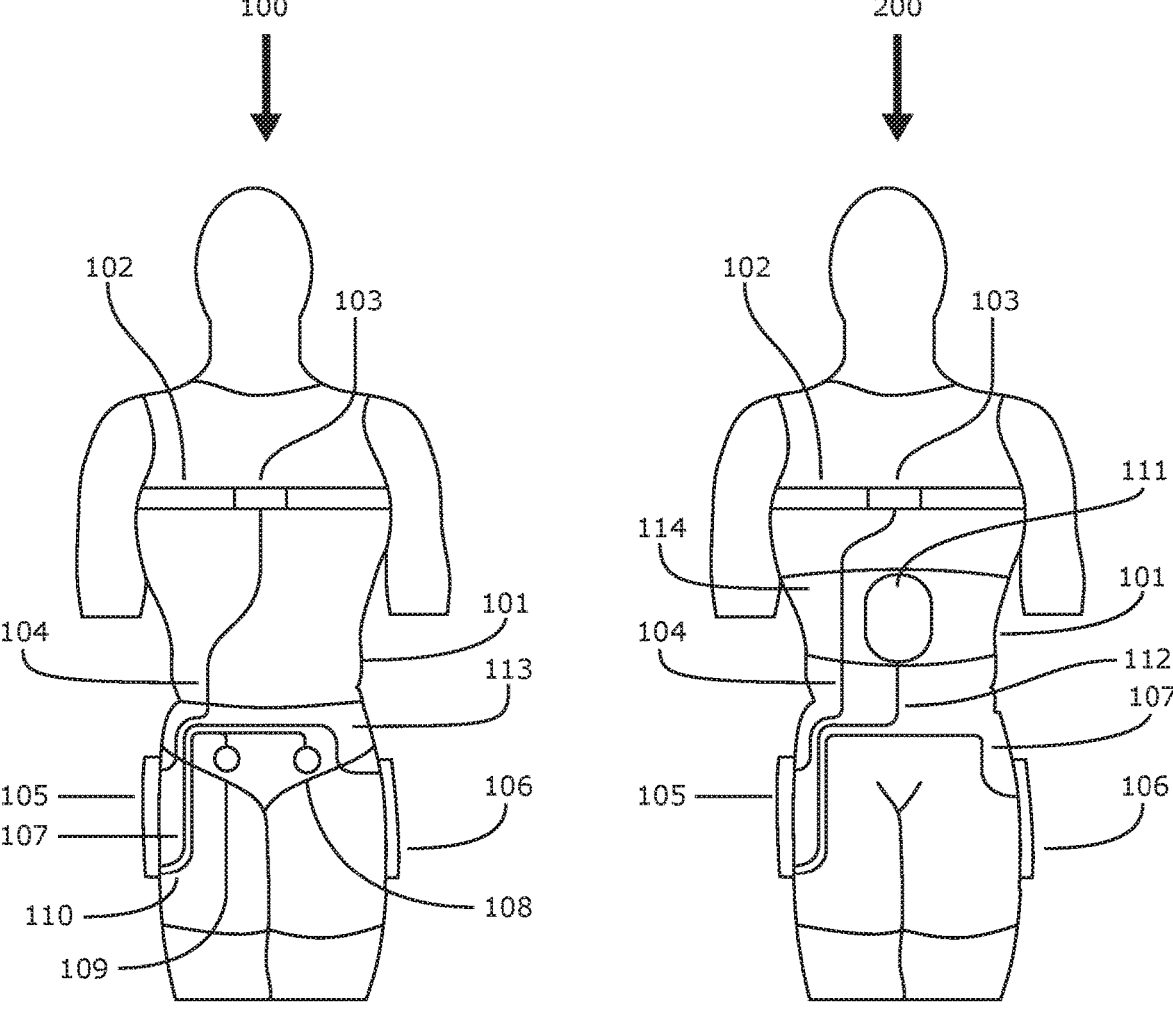
FIGS. 1A and 1B show an external front view of embodiments of a hernia device system worn on a user.

FIG. 1A is a front view of an exemplary embodiment of a hernia device or system 100 intended to manage and/or prevent the formation of inguinal hernias, including a wearable garment 101, a sensing mechanism (i.e., sensor) 103 attached to a flexible band 102, a controller 105, a power source 106, and pressure applicators 108 and 109. The flexible band 102 may be attached to the garment 101 in a permanent or removable manner using methods known to the art including, but not limited to sewing, hook-and-loop fasteners, hooks and eye closures, toggle closures, ties, cord laced through grommets, zippers, snaps, buttons, buckles, side-release buckles, pockets, combinations thereof, and the like. The sensor 103 may be permanently or reversibly attached to flexible band 102 using methods known to the art including, but not limited to sewing, hook-and-loop fasteners, hooks and eye closures, toggle closures, ties, cord laced through grommets, zippers, snaps, buttons, buckles, side-release buckles, pockets, combinations thereof, and the like.

Similarly, the controller 105 and power source 106 may be permanently or reversibly attached to the garment 101 using methods known to the art including, but not limited to, sewing, hook-and-loop fasteners, hooks and eye closures, toggle closures, ties, cord laced through grommets, zippers, snaps, buttons, buckles, side-release buckles, combinations thereof, and the like. Alternatively, controller 105 and power source 106 may be held within a pocket or pockets (not shown) formed in the garment 101. The controller 105 and power source 106 may also be combined and packaged as a single unit with added design elements that allow power source management (e.g., replacing or recharging a battery). The sensor 103 is connected to the controller 105 via one or more wires 104 capable of carrying electrical and/or telecommunication signals from the sensor 103 to the controller 105. Alternatively, the signals produced by sensor 103 may be wirelessly transmitted to controller 105, e.g., using Bluetooth technology. The wire 104 may be permanently or reversibly attached to the sensor 103 and controller 105 using connections or joining methods known to the art including, but not limited to bonding, welding, ultrasonic welding, soldering, crimping, press or interference fits, banana plugs, spade and pin connectors, coaxial cable connectors (e.g., F, N, sub-miniature version A, SMB, SMC, bayonet Neill-Concelman, threaded Neill-Concelman, twin BNC, triaxial, and the like), universal serial bus (USB) connectors, HDMI connectors, RS232 connectors, combinations thereof, and the like.

The controller 105 may be connected to the power source 106 via one or more wires 107 capable of carrying an electrical and/or telecommunication signal. The wire 107 may be permanently or reversibly attached to controller 105 and power source 106 using connections or joining methods known to the art including, but not limited to bonding, welding, ultrasonic welding, soldering, crimping, press or interference fits, banana plugs, spade and pin connectors, coaxial cable connectors (e.g., F, N, sub-miniature version A, SMB, SMC, bayonet Neill-Concelman, threaded Neill-Concelman, twin BNC, triaxial, and the like), universal serial bus (USB) connectors, HDMI connectors, RS232 connectors, combinations thereof, and the like.

The pressure applicators 108, 109 are located on the garment 101 at predetermined locations intended to position the applicators 108, 109 over the inguinal rings of the user, and may be permanently or reversible attached to the garment 101 using methods known to the art including, but not limited to sewing, hook-and-loop fasteners, hooks and eye closures, toggle closures, ties, cord laced through grommets, zippers, snaps, buttons, buckles, side-release buckles, pockets, combinations thereof, and the like. The pressure applicators 108 and 109 are connected to the controller 105 via connecting element 110. The connecting element 110 may be permanently or reversibly joined to the controller 105 and/or pressure applicators 108 and 109 using methods known to the art including, but not limited to bonding, welding, ultrasonic welding, over-molding, threading/tapping, crimping, crimping, press or interference fits, banana plugs, spade and pin connectors, coaxial cable connectors (e.g., F, N, sub-miniature version A, SMB, SMC, bayonet Neill- Concelman, threaded Neill-Concelman, twin BNC, triaxial, and the like), universal serial bus (USB) connectors, HDMI connectors, RS232 connectors, combinations thereof, and the like.

The form and structure of connecting element 110 will be suited to the particular mechanism utilized in each of the pressure applicators 108, 109. For example, if the pressure applicators 108, 109 include a hydraulic system for applying pressure and an electronic system for controlling flow of the hydraulic fluid (not shown), connecting element 110 will be fabricated of a material and of a form (e.g., tubing, pipe, and the like) that can support fluid flow at the requisite pressure. Optionally, a tubular connecting element may further include one or more additional lumens or passages, e.g., to receive one or more wires or other elements for conducting electrical current.

In another example, if the pressure applicators 108, 109 include linear solenoids, the connecting element 110 suited for the system would be the type or form that is capable of transmitting electrical and/or telecommunication signal between the controller 105 and the pressure applicators 108, 109. Alternatively (not shown), the electrical components joining the various other components of the system may be connected using separate, isolated conduits or wiring. This may be useful if minimization of interference between the electromagnetic fluids generated by the various system components is a key feature of the system. Furthermore, separating the electrical components of the system from, for example, the hydraulic or pneumatic components of the system may increase the safety and reliability of the system.

Optionally, a stabilizer 113 may be added as a separate component of the hernia system 100 or may be integrated with the wearable garment 101. The stabilizer 113 may be fabricated in the form of a belt, trusses, briefs, and the like and may be made of flexible but non-compliant materials (i.e., does not stretch) and/or maintains its shape and/or dimensions during use. The stabilizer 113 generally provides structural support over pressure applicators 108, 109 such that when the pressure applicators 108, 109 are activated (i.e., expanded or extended to apply counteractive pressure against the treatment zone), the applied inward forces are transmitted with minimal loss to counteract the outward force generated by the body that could cause herniation over the treatment zone or anatomy.

FIG. 1B is a front view of another exemplary embodiment of a hernia device or system 200 intended to manage and/or prevent the formation of ventral hernias, including a wearable garment 101, a sensor 103 attached to a flexible band 102, a controller 105, a power source 106, and a pressure applicator 111. The descriptions of common components of system 100 and 200 having the same reference number are generally the same. The pressure applicator 111 is located over the ventral area of the user, and may include electromagnetic, pneumatic, hydraulic, or mechanical components for applying pressure, or combinations thereof.

The pressure applicator 111 is connected to the controller 105 via a connecting element 112. The connecting element 112 may be permanently or reversibly joined to the controller 105 and/or pressure applicator 111 using methods known to the art including, but not limited to bonding, welding, ultrasonic welding, over-molding, threading/tapping, crimping, press or interference fits, banana plugs, spade and pin connectors, coaxial cable connectors (e.g., F, N, sub-miniature version A, SMB, SMC, bayonet Neill-Concelman, threaded Neill-Concelman, twin BNC, triaxial, and the like), universal serial bus (USB) connectors, HDMI connectors, RS232 connectors, combinations thereof, and the like. The form and structure of the connecting element 112 will be suited to the particular mechanism utilized in the pressure applicator 111.

For example, if the pressure applicator 111 includes a hydraulic system for applying pressure and an electronic system for controlling flow of the hydraulic fluid (not shown), the connecting element 112 may be fabricated from a material and form (e.g., tubing, pipe) that can support fluid flow at the requisite pressure and, optionally, may further include one or more additional lumens or passages that can accept a wire or other element for conducting electrical current. In another example, if the pressure applicator 111 includes linear solenoids, the connecting element 112 suited for the system would be the type or form that is capable of transmitting electrical load and/or telecommunication signal between controller 105 and pressure applicator 111.

Alternatively (not shown), the electrical components joining the various other components of the system may be connected using separate, isolated conduits or wiring. This may be useful if minimization of interference between the electromagnetic fluids generated by the various system components is a key feature of the system. Furthermore, separating the electrical components of the system from, for example, the hydraulic or pneumatic components of the system may increase the safety and reliability of the system.

Optionally, a stabilizer 114 may be added as a separate component of the hernia system 200 or may be integrated with the wearable garment 101. The stabilizer 114 may be fabricated in the form of a belt, trusses, and the like and may be made of flexible but non-compliant materials (i.e., does not stretch) and maintains its shape and/or dimensions during use. The stabilizer 114 generally provides structural support over pressure applicator 111 such that when the pressure applicator 111 is activated (i.e., expanded or extended to apply counteractive pressure against the treatment zone), the applied inward force is transmitted with minimal losses to counteract the outward force generated by the body that could cause herniation over the treatment zones or anatomy.

Figure 2:
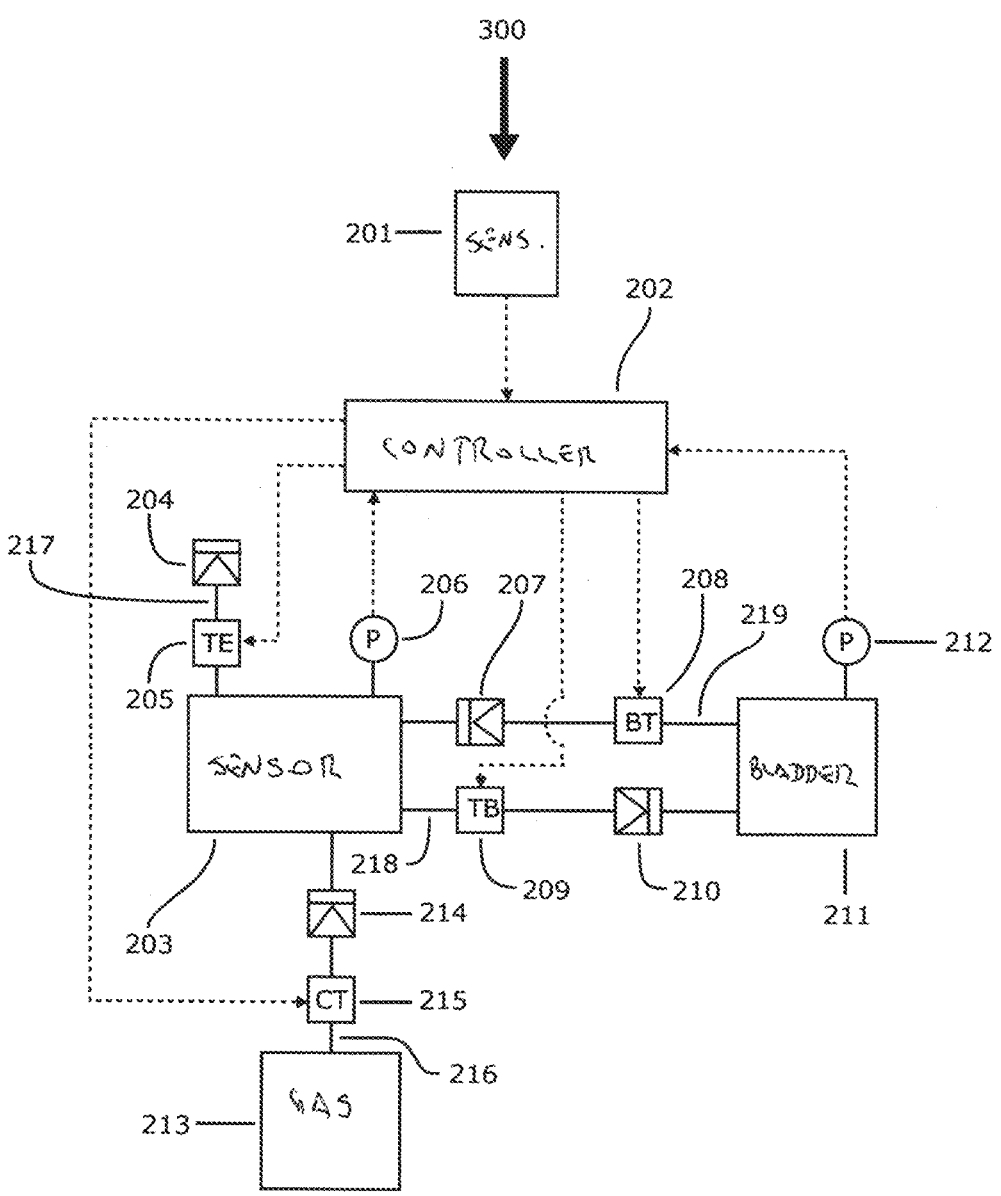
FIG. 2 is a schematic illustration of components and electronic, pneumatic, and hydraulic linkages of an exemplary embodiment of a hernia device or system.

FIG. 2 is a schematic illustration of an embodiment of a configuration of a hernia device or system 300 that may be included in the systems 100, 200. In this illustration, solid lines represent a connection between components that enables fluid communication between the components, and dashed lines with arrows represent an electrical connection between components with the arrow signifying the direction in which information is transmitted. One-way valves are symbolized by a square box with an arrow and a line perpendicular to the orientation of the arrow drawn within the box. The arrow indicates the direction in which flow is permitted. It should be noted that a power supply is not shown, nor are the various connections between the power supply and the other system components that require power. It should be evident to one of skill in the art that a number of devices for producing and transmitting power are readily available and may be incorporated into the system 300.

In the embodiment shown in FIG. 2, the hernia device system 300 generally includes a canister 213 filled with pressurized gas that is used to drive a hydraulic pump 203 which then transfers the hydraulic fluid (not shown) into an expandable bladder 211 in response to a controller 202 receiving a signal from sensor 201 that meets a set of pre-determined requirements or parameters. The gas canister 213 is in communication with the hydraulic pump 203 via fluid line 216 (e.g., tubing, pipe, and/or other conduit) and connected in between is a gas canister valve 215 (e.g., using a solenoid valve, a valve activated by an actuator, and the like) and a one-way valve 214 that are in series with each other. Alternatively, the gas canister valve 215 itself may be a one-way type of valve, eliminating the one-way valve 214. The gas canister valve 215 is connected to and controlled by the controller 202.

Hydraulic pump 203 further includes a pressure sensor 206 and a vent mechanism 217 that purges excess gas pressure supplied by the canister 213. The vent mechanism 217 includes a vent valve 205 (e.g., a solenoid valve, a valve activated by an actuator, and the like) and a one-way valve 204 that are in series with each other. Alternatively, the vent valve 205 itself may be a one-way type of valve, eliminating the one-way valve 214. The vent valve 205 is connected to and controlled by the controller 202. Optionally, a membrane or filter (not shown) that is permeable to gas but impermeable to the hydraulic fluid (not shown) may be located in series with the vent valve 205 and the one-way valve 204.

The pressure sensor 206 is connected to the controller 202 and feeds pressure signals corresponding to the hydraulic pressure reading within the hydraulic pump 203 to the controller 202. The hydraulic pump 203 is connected to the expandable bladder 211 via fluid line 218 (e.g., tubing, pipe, and/or other conduit) and connected in between is a pump valve 209 (e.g. a solenoid valve, a valve activated by an actuator, and the like) and a one-way valve 210 that are in series with each other. Alternatively, the pump valve 205 itself may be a one-way type of valve, eliminating the one-way valve 210. The pump valve 209 is connected to and controlled by the controller 202. The expandable bladder 211 further includes a pressure sensor 212 that is connected to the controller 202 and transmits the pressure signals corresponding to the hydraulic pressure reading within the expandable bladder 211 to the controller 202. The expandable bladder 211 is connected to the hydraulic pump 203 via a return fluid line 219 (e.g., tubing, pipe, and/or other conduit) and connected in between is a bladder valve 208 (e.g. a solenoid valve, a valve activated by an actuator, and the like) and a one-way valve 207 that are in series with each other. Alternatively, the bladder valve 208 itself may be a one-way type of valve, eliminating the one-way valve 207. The bladder valve 208 is connected to and controlled by the controller 202.

The hernia system 300 may operate by selectively applying pre-determined pressure to activate the expandable bladder 211 as a response to a pre-determined signal from the sensor 201. For example, the user may inhale deeply prior to attempting an athletic movement or act. The increase in girth dimension (i.e., perimeter of upper chest) may change the signals from the sensor 201 that are sent to the controller 202, which the controller 202 may identify and, in turn, cause the gas canister switch (not shown) to trigger the gas canister valve 215 to open the gas canister valve (not shown) to drive the hydraulic pump 203 and pressurizes the incompressible fluid contained within the hydraulic pump 203.

Optionally, the controller 202 may regulate the pressure within the hydraulic pump 203 by comparing the tank pressure as reported by the pump pressure sensor 206 to a pre-selected set point. If the pressure exceeds the set point, the controller 202 may close the gas canister valve 215 and open the vent valve 205 to vent a portion of the gas to the environment and reduce the tank pressure. The controller 202 may use a negative feedback loop to quickly adjust the tank pressure to the specified set point, or into a band of acceptable pressure values about the set point. The controller 202 may then close the corresponding valve of the gas canister valve 215 and vent valve 205 to isolate the hydraulic pump 203 from the gas canister 213 and the ambient environment.

The pump valve 209 may then be opened to allow flow of the incompressible fluid from the hydraulic pump 203 into the expandable bladder 211. The controller 202 may optionally regulate the pressure within the expandable bladder 211 by comparing the bladder pressure based on pressure signals from the bladder pressure sensor 212 to a pre-selected set point. If the pressure exceeds the set point, the controller 202 may close the pump valve 209 and open the bladder valve 208 to return a portion of the incompressible fluid to the hydraulic pump 203 and reduce the pressure in the expandable bladder 211. The controller 202 may use a negative feedback loop to quickly adjust the pressure in the expandable bladder 211 to the specified set point, or into a band of acceptable pressure values about the set point.

Once the treatment duration has been met, the controller 202 may open the bladder valve 208 and vent valve 205 to permit the pressurized hydraulic fluid (not shown) to return to the hydraulic pump 203 and purge the pressurized gas to the environment.

The expandable bladder 211 may be positioned as needed to manage or prevent a number of different hernias, such as inguinal, ventral, umbilical, or Spigelian. It should be clear to one of skill in the art that while this example utilizes a single hydraulic pump 203 and a single expandable bladder 211, systems with multiple hydraulic pump 203 and/or multiple expandable bladder 211 may be used in particular applications. For example, to mitigate or prevent inguinal hernias, a system may be used that includes two hydraulic pumps 203 and two expandable bladders 211 in pairs, with each expandable bladder 211 situated to apply direct pressure about the right or left inguinal ring, respectively (not shown). This configuration may enable the controller 202 to set differing levels of pressure for each expandable bladder 211, if desired by the user.

Alternatively, a system may be used to mitigate or prevent inguinal hernias that includes a single hydraulic pump 203 and two expandable bladder 211, with each expandable bladder 211 situated to apply direct pressure to the right or left inguinal ring, respectively, (not shown) but supplied by the same source of hydraulic fluid. It should also be clear to one of skill in the art that various configurations and arrangements of gas canisters, hydraulic pumps, and expandable bladders in series configurations, parallel configurations, or a combination thereof may be envisioned.

For example, an alternative embodiment of the hernia system 300 may provide a base level of hydraulic pressure in the absence of a triggering signal, yet is capable of providing a second, elevated level of hydraulic pressure in response to a signal received by the sensor, such as a sufficient expansion of the diaphragm/ribcage.

Figure 3:
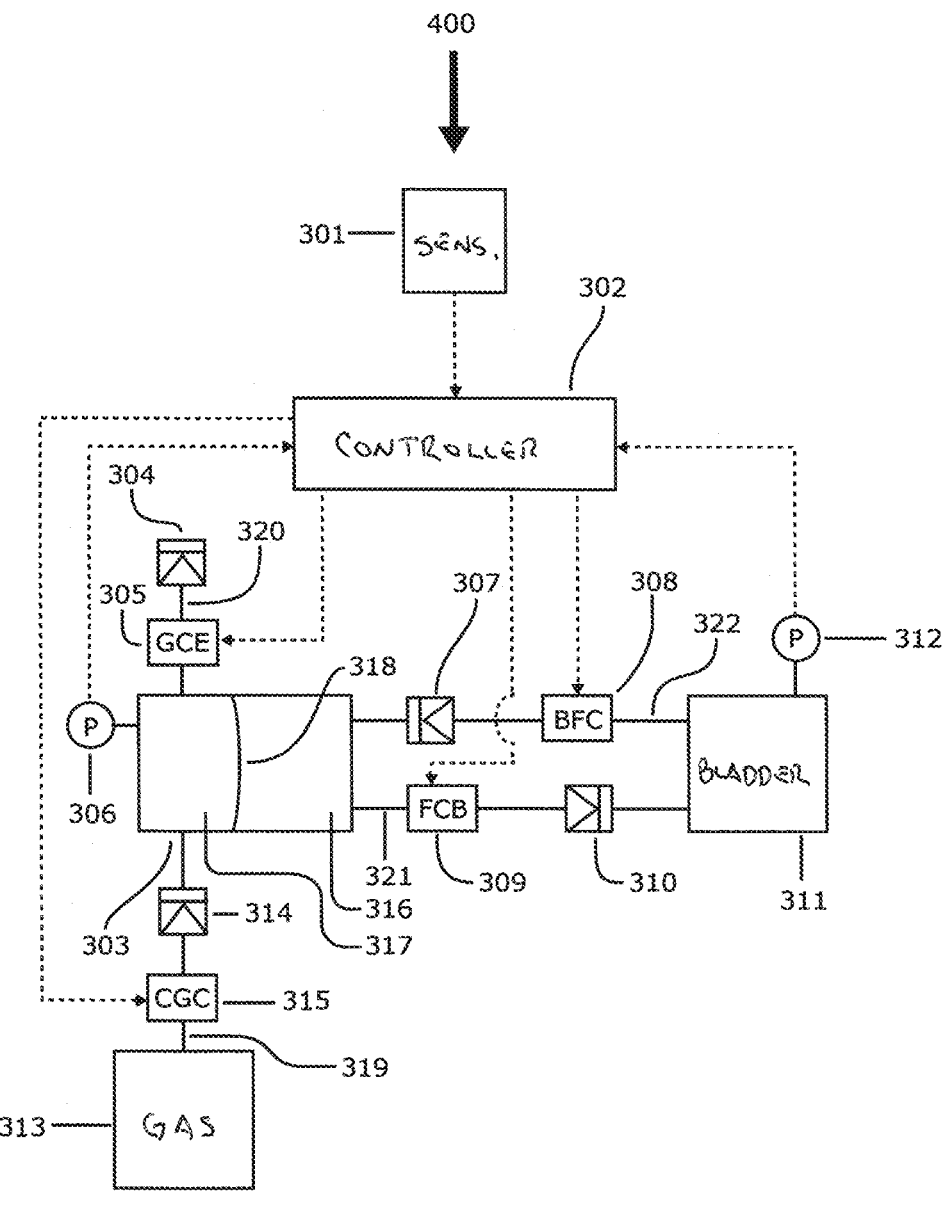
FIG. 3 is a schematic illustration of components and electronic, pneumatic, and hydraulic linkages of another exemplary embodiment of a hernia device or system.

FIG. 3 is a schematic illustration of another embodiment of a hernia device or system 400. Similar to the previous embodiments, solid lines represent a connection between components that enables fluid communication between the components, and dashed lines with arrows represent an electrical connection between components with the arrow signifying the direction in which information is transmitted. One-way valves are symbolized by a square box with an arrow and a line perpendicular to the orientation of the arrow drawn within the box. The arrow indicates the direction in which flow is permitted.

It should be noted that a power supply is not shown, nor are the various connections between the power supply and the other system components that require power. It should be evident to one of skill in the art that a number of methods for producing and transmitting power are readily available and may be incorporated into the system 400.

In the embodiment shown in FIG. 3, the hernia system 400 generally includes a gas canister 313 filled with pressurized gas that is used to drive the hydraulic unit 303, which then transfers the hydraulic fluid (not shown) into an expandable bladder 311 in response to a controller 302 receiving a signal from sensor 301 that meets a set of pre-determined requirements or parameters. The hydraulic unit 303 is divided into two cells by an elastic, gas impermeable membrane 318. One side of the membrane includes a gas cell 317 and the other side includes a fluid cell 316. The fluid cell 316 contains a hydraulic fluid (not shown) that is used to expand the expandable bladder 311. The gas canister 313 is in communication with the gas cell 317 via fluid line 319 (e.g., tubing, pipe, and/or other conduit) and connected in between is a gas canister valve 315 (e.g., a solenoid valve, a valve activated by an actuator, and the like) and a one-way valve 314 that are in series with each other. Alternatively, the gas canister valve 315 itself may be a one-way type of valve, eliminating the one-way valve 314.

The gas canister valve 315 is connected to and controlled by the controller 302. The gas cell 317 further includes a pressure sensor 306 and a vent mechanism 320 that purges excess gas pressure supplied by the canister 313. The vent mechanism 320 includes a vent valve 305 (e.g., a solenoid valve, a valve activated by an actuator, and the like) and a one-way valve 304 that are in series with each other. Alternatively, the vent valve 305 itself may be a one-way type of valve, eliminating the one-way valve 304. The vent valve 305 is connected to and controlled by controller 302. The pressure sensor 306 is connected to the controller 302, which provides signals proportional to the amount of gas pressure within the gas cell 317 to the controller 302. The fluid cell 316 is in communication with the expandable bladder 311 via fluid line 321 (e.g., tubing, pipe, and/or other conduit) and connected in between is a fluid cell valve 309 (e.g., a solenoid valve, a valve activated by an actuator, and the like) and a one-way valve 310 that are in series with each other. Alternatively, the fluid cell valve 309 itself may be a one-way type of valve, eliminating the one-way valve 310. The fluid cell valve 309 is connected to and controlled by the controller 302. Expandable bladder 311 further comprises a pressure sensor 312 that is connected to controller 302 and transmits the pressure reading within expandable bladder 311 to controller 302.

A return fluid line 322 (e.g. tubing, pipe) connects the expandable bladder 311 to the fluid cell 316 and in between is a bladder valve 308 (e.g., a solenoid valve, a valve activated by an actuator, and the like) and a one-way valve 307 that are in series with each other. Alternatively, the bladder valve 308 itself may be a one-way type of valve, eliminating the one-way valve 307. The bladder valve 308 is connected to and controlled by controller 302.

The embodiment of the hernia device system 400 may be operated by selectively applying predetermined pressure to activate the expandable bladder 311 as a response to a predetermined signal from the sensor 301. For example, the user may inhale deeply prior to attempting an athletic movement or act. The increase in girth dimension (i.e., perimeter of upper chest) may cause the controller 302 to identify a change in signals from the sensor 301, and, consequently, the controller 302 activate the gas canister switch (not shown) to trigger the gas canister valve 315 to open the gas canister valve (not shown) and pressurize the gas cell 317. The controller 302 may optionally regulate the pressure within the gas cell 317 by comparing the gas cell pressure as reported by the gas cell pressure sensor 306 to a pre-selected set point. If the pressure exceeds the set point, the gas canister valve 315 may be closed and the vent valve 305 opened to purge excess gas to the environment and adjust the gas pressure within gas cell 317. The controller 302 may use a negative feedback loop to quickly adjust the pressure within the gas cell 317 to the specified set point, or into a band of acceptable pressure values about the set point. The controller 302 may then close the gas canister valve 315 and vent valve 305 to isolate the gas cell 317 from the gas canister 313 and the ambient environment.

The fluid cell valve 309 may then be opened, enabling the elastic membrane 318 bisecting the hydraulic unit 303 to expand under the elevated pressure in the gas cell 317. The expansion of the elastic membrane 318 forces the incompressible fluid (not shown) to flow from the fluid cell 316 into the expandable bladder 311. The controller 302 may optionally regulate the pressure within the expandable bladder 311 by comparing the bladder pressure as reported by the bladder pressure sensor 312 to a pre-selected set point. If the pressure exceeds the set point, the fluid cell valve 309 may be closed and the bladder valve 308 opened to return a portion of the incompressible fluid (not shown) to the fuel cell 316 and reduce the pressure in the expandable bladder 311. The controller 302 may use a negative feedback loop to quickly adjust the pressure within the expandable bladder 311 to the specified set point, or into a band of acceptable pressure values about the set point.

Once the treatment duration has been met, the controller 302 may open bladder valve 308 and vent valve 305 to vent the pressurized gas within the gas cell 317 to the environment and permit the hydraulic fluid (not shown) to return to fluid cell 316.

The expandable bladder 311 may be positioned as needed to manage or prevent a number of different hernias, such as inguinal, ventral, umbilical, or Spigelian. It should be clear to one of skill in the art that, while this example utilizes a single hydraulic unit 303 and a single expandable bladder 311, systems with multiple hydraulic unit 303 and/or multiple expandable bladder 311 may be used in particular applications. For example, the management of preventing inguinal hernias may be configured using a system with two hydraulic unit 303 and two expandable bladder 311 in pairs, with each expandable bladder 311 situated to apply direct pressure about the right or left inguinal ring (not shown). This configuration may enable the controller to set differing levels of pressure for each expandable bladder 311, if desired by the user. Alternatively, the management of preventing inguinal hernias may be configured using a system with a single hydraulic unit 303 and two expandable bladder 311, with each expandable bladder 311 situated to apply direct pressure to the right or left inguinal ring (not shown) but supplied by the same source of hydraulic fluid (not shown).

It should also be clear to one of skill in the art that various configurations and arrangements of gas canisters, hydraulic unit, and expandable bladders in series configurations, parallel configurations, or a combination thereof may be envisioned. For example, a hernia device system 400 may be envisioned to provide a base level of hydraulic pressure in the absence of a triggering signal, but is capable of providing a second, elevated level of hydraulic pressure in response to a signal received by the sensor, such as a sufficient expansion of the diaphragm/ribcage.

In alternative embodiments, the systems herein may generate one or more outputs to the target locations of the user's body, e.g., instead of or in addition to, physical pressure. For example, the system may include an electromechanical device configured to generate signals to stimulate tissue at the target location, e.g., to prevent muscle contraction when activated. Alternatively, the electromechanical device may be configured to generate signals to stimulate tissue at the predetermined location to induce muscle contraction, to induce muscle relaxation when activated, and the like.

In another alternative, the system may include one or more ultrasound transducers configured to apply pressure to the predetermined location when activated. In yet another alternative, the system may include a transcutaneous nerve stimulation device configured to cause muscle paralysis to neutralize contraction at the predetermined location. In still another alternative, the system may include a device configured to generate and apply heating or cooling when activated. It will be appreciated that one or more of pressure, stimulation, heating, and/or cooling may be delivered by the system simultaneously or sequentially based on the desired treatment.

Optionally, the controller or an external device communicating with the controller may use artificial intelligence and/or machine learning to modify operation of the system, e.g., generating one or more interventions for hernia and other injuries using various modalities. For example, a remote electronic device may communicate with the controller to receive data from the system for analysis by the electronic device. The resulting analysis may be used to modify operation of the system and/or to advise the user and/or their caregivers, e.g., medical professionals, sports trainers, and the like.

As described elsewhere herein, the components of the system may be incorporated into a variety of garments and/or other wearable devices, e.g., carried on a single garment or on multiple garments worn by the user. In exemplary embodiments, the garment may include one or more of a jersey, a shirt, a singlet, a tracksuit, a swimsuit, a wet suit, a leotard, a bodysuit, a jockstrap, a sports bra, and a pair of shorts. It will be appreciated that the systems herein may be incorporated into sportswear specifically configured to allow the user to perform various sports activities, e.g., wrestling, boxing, swimming, cycling, and the like, while minimizing interference by the components carried by the garment. Alternatively, the garment may be configured to be worn by a patient, e.g., being treated for a hernia, in a home or medical care facility, while allowing the patient to be ambulatory.

In addition, although the systems and methods herein have been described as having particular application in mitigating and/or preventing hernias, it will be appreciated that the systems and methods may be used for other anatomies and/or conditions, e.g., for mitigating and/or preventing other musculoskeletal injuries. For example, output devices, e.g., applying localized pressure, stimulation, and the like, may be provided at a variety of locations on a wearable device to provide localized treatment and/or preventive condition to desired mitigation or treatment sites on a user's body. In exemplary embodiments, depending on the activity, an output device may be provided at one or more locations on the user's neck, hip, spine, shoulders, upper arms, lower arms, wrist, hand, fingers, upper legs, lower legs, ankles, feet, and the like, to apply pressure, stimulation, and the like to the locations when a predetermined activity is identified.

In an exemplary embodiment, a swimmer may wear a garment that includes one or more sensors to monitor physical parameters of the swimmer and one or more output devices located on the garment to apply pressure, stimulation, and/or other outputs to desired localized sites on the swimmer's body, e.g., the swimmer's shoulders, back, arms, hips, and/or legs, when the sensors indicate that the swimmer is engaged in a predetermined physical activity, e.g., swimming generally or swimming particular strokes that require additional support to specific localized sites. In another example, a user sitting at a desk working may wear a device having outputs devices located at the user's neck, spine, wrist, and/or other mitigation sites, e.g., applying pressure if the system identifies the user's posture is slouched or otherwise undesirable, e.g., to prevent exacerbating or causing an injury at the sites. In still another example, a user with a back injury may wear the system while sleeping and the system may activate one or more output devices if it indicates that the user is sleeping in a position that may exacerbate the injury. FIG. 4 includes a list of exemplary physical activities and respective application sites (e.g., indicated by "1") where pressure, stimulation, and/or other outputs may be applied to provide localized treatment, e.g., using any of the systems and methods described elsewhere herein.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A system for mitigating or preventing a hernia or other musculoskeletal injuries, comprising:

a wearable device configured to be worn on a user;

one or more sensors configured to generate signals corresponding to one or more physical parameters of the user;

a controller coupled to the one or more sensors to receive the signals, the controller configured to identify when the user inhales sufficiently to indicate the user is about to perform a predetermined physical activity based at least in part on the signals; and an output device carried on the wearable device at a predetermined location corresponding to a target hernia mitigation site on the user's body adjacent an inguinal zone or groin of the user, the controller communicating with the output device and configured to activate the output device when the processor determines that the predetermined physical activity is about to be performed to provide an output to mitigate a hernia or prevent a hernia from occurring at the mitigation site, wherein the output device comprises a pressure applicator configured to apply pressure to the mitigation site when activated by the controller.

2. The system of claim 1, wherein the wearable device comprises a garment.

3. The system of claim 2, wherein the garment is configured to at least partially surround the user's torso.

4. The system of claim 2, wherein the garment is configured to at least partially cover the user's abdomen.

5. The system of claim 4, wherein the garment is configured to overlie an inguinal ring of the user.

6. The system of claim 2, wherein one or more of the one or more sensors, the controller, and the output device are removably mounted to the garment.

7. The system of claim 2, wherein the garment comprises one of a jersey, a shirt, a singlet, a tracksuit, a swimsuit, a wet suit, a leotard, a bodysuit, a jockstrap, a sports bra, and a pair of shorts.

8. The system of claim 1, wherein the one or more sensors comprise a sensor configured to generate the signals by measuring a change in physical dimension of the torso during respiration.

9. The system of claim 1, wherein the one or more sensors comprise a sensor configured to generate the signals by measuring a force exerted by one or more muscles of the user during respiration.

10. The system of claim 8, wherein the one or more sensors further comprise a band configured to wrap at least partially around the user's torso, wherein the sensor is carried on the band.

11. The system of claim 1, wherein the one or more sensors further comprise a band configured to wrap at least partially around the user's torso, the band configured to generate electrical signals in response to changes in physical dimension of a region of the torso during respiration to generate the signals.

12. The system of claim 11, wherein the band comprises a pressure sensitive conductive sheet that changes resistance during respiration as the user's torso expands and contracts, the signals based at least in part on changes in the resistance.

13. The system of claim 11, wherein a strength of the electrical signals is proportional to a relative expansion of one of the user's ribcage and the user's diaphragm.

14. The system of claim 1, wherein the one or more sensors comprise a capnometer configured to generate the signals responsive to the user's breathing.

15. The system of claim 1, wherein the one or more sensors comprise a sensor configured to generate the signals based on changes in a biochemical parameter of the user.

16. The system of claim 15, wherein the biochemical parameter comprises one of skin temperature and sweat generation of the user.

17. The system of claim 1, wherein the one or more sensors comprise a sensor configured to generate the signals responsive to respiratory or blood gases of the user.

18. The system of claim 1, wherein the one or more sensors comprise a sensor configured to generate the signals responsive to gas exchange sensed through the user's skin.

19. The system of claim 1, wherein the pressure applicator comprises:

a pumping mechanism coupled to the controller; and an expandable device configured to expand to apply the pressure to the mitigation site when activated.

20. A system for mitigating or preventing a hernia, musculoskeletal injuries, or other medical conditions, comprising:

a wearable device configured to be worn on a user;

one or more sensors configured to generate signals corresponding to one or more physical parameters of the user;

a controller coupled to the one or more sensors to receive the signals, the controller configured to identify when the user is about to perform a predetermined physical activity based on the signals; and an output device carried on the wearable device at a predetermined location corresponding to a target mitigation site on the user's body, the controller communicating with the output device and configured to activate the output device when the predetermined physical activity is identified to provide an output to mitigate or prevent a hernia or other injury from occurring at the mitigation site, wherein the output device comprises a pressure applicator positioned on the wearable device at a location corresponding to an inguinal zone or groin of the user, and wherein the controller is configured to activate the pressure applicator to apply pressure to the inguinal zone or the groin.

21. The system of claim 20, wherein the pressure applicator comprises:

a pumping mechanism coupled to the controller; and an expandable device configured to expand to apply the pressure to the inguinal zone or the groin when activated.

22. The system of claim 20, wherein the pressure applicator comprises:

a reservoir containing a fluid;

a bladder on the garment at a location corresponding to the inguinal zone or groin of the user; and a valve operatively coupled to the controller such that, when the controller identifies an activation signal in the signals identifying when the user is about to perform a predetermined physical activity, the controller is configured to open the valve to deliver the fluid from the reservoir into the bladder to expand the bladder to apply pressure to the inguinal zone or groin of the user.

23. The system of claim 22, wherein the controller is configured to close the valve after expanding the bladder to maintain the bladder at a desired bladder pressure for a set amount of time.

24. The system of claim 1, wherein the pressure applicator comprises:

a reservoir containing a fluid;

a bladder on the garment at a location corresponding to the inguinal zone or groin of the user; and a valve operatively coupled to the controller such that, when the controller identifies an activation signal in the signals identifying when the user is about to perform a predetermined physical activity, the controller is configured to open the valve to deliver the fluid from the reservoir into the bladder to expand the bladder to apply pressure to the inguinal zone or groin of the user.

25. The system of claim 24, wherein the controller is configured to close the valve after expanding the bladder to maintain the bladder at a desired bladder pressure for a set amount of time.

* * * * *